(12) United States Patent
Gainza Lafuente et al.

(10) Patent No.: US 9,919,027 B2
(45) Date of Patent: Mar. 20, 2018

(54) LIPID NANOPARTICLE OF POLYMYXIN (71) Applicants: BIOPRAXIS RESEARCH AIE, Alava (ES); PRAXIS PHARMACEUTICAL, S.A., Alava (ES); FUNDACIO D'INVESTIGACIO SANITARIA DE LES ILLES BALEARS, Palma (ES); UNIVERSIDAD DEL PAIS VASCO/EUSKAL HERRIKO UNIBERTSITATEA, Leioa (ES); UNIVERSIDAD DE BARCELONA, Barcelona (ES); CONSEJO SUPERIOR DE INVESTIGACIONES CIENTIFICAS, Madrid (ES)

(72) Inventors: Eusebio Gainza Lafuente, Alava (ES); Angel Del Pozo Perez, Alava (ES); Garazi Gainza Lucea, Alava (ES); Oihane Ibarrola Moreno, Alava (ES); Silvia Villullas Rincon, Alava (ES); Raul Fernandez Plagaro, Alava (ES); Daniel Bachiller Perez, Madrid (ES); Jose Luis Pedraz Munoz, Leioa (ES); Amaya Esquisabel Alegria, Leioa (ES); Marta Pastor Navarro, Leioa (ES); Ester Fuste Dominguez, Barcelona (ES); Eulalia Sans Serramit Jana, Barcelona (ES); Iraida Gil Martin, Barcelona (ES)

(73) Assignees: Biopraxis Research Aie, Alava (ES); Praxis Pharmaceutical, S.A., Alava (ES); Fundacio D'Investigacio Sanitaria De Les Illes Balears, Palma (ES); Universidad Del Pais Vasco/Euskal Herriko Unibertsitatea, Leioa (ES); Universidad De Barcelona, Barcelona (ES); Consejo Superior De Investigaciones Cientificas, Madrid (ES)

( * ) Notice: Subject to any disclaimer, the term of this patent is extended or adjusted under 35 U.S.C. 154(b) by 0 days.

(21) Appl. No.: 14/985,532

(22) Filed: Dec. 31, 2015

(65) Prior Publication Data
US 2016/0113995 A1 Apr. 28, 2016

Related U.S. Application Data (63) Continuation of application No. PCT/ES2014/070538, filed on Jul. 2, 2014.

(30) Foreign Application Priority Data

Jul. 3, 2013 (EP) ................................ 13382268

(51) Int. Cl.
 A61K 38/12 (2006.01)
 A61K 9/00 (2006.01)
 A61K 9/51 (2006.01)

(52) U.S. Cl.
 CPC ............ *A61K 38/12* (2013.01); *A61K 9/0073* (2013.01); *A61K 9/5123* (2013.01)

(58) Field of Classification Search
 CPC ............... A61K 9/14; A61K 9/51; A61K 9/50
 See application file for complete search history.

(56) References Cited

U.S. PATENT DOCUMENTS

| 6,653,319 B1 * | 11/2003 | Xiang | .................. | C07D 491/22 |
| | | | | 514/283 |
| 2006/0222716 A1 * | 10/2006 | Schwarz | .............. | A61K 9/5123 |
| | | | | 424/489 |
| 2009/0169635 A1 | 7/2009 | Schwarz et al. | | |

FOREIGN PATENT DOCUMENTS

| EP | 1129705 A1 | 9/2001 | | |
| WO | WO 2011116963 A2 * | 9/2011 | ........... | A61K 8/0283 |
| WO | 2012061902 A1 | 5/2012 | | |

OTHER PUBLICATIONS

Cremophor® EL has a melting point of 4° C.; See Spectrum, "Cremophor® EL-Material Safety Data Sheet", 2008, pp. 1-6.*
Suppocire® CM has a melting point of 38.0-40.0° C.; See Gattefosse, "Suppocire® CM Pellets", 2010, pp. 1-2.*
Tyloxapol® is a non-ionic surfactant; See Sigma-Adrich, "Tyloxapol®-Production Specification", Obtained from www.sigmaaldrich.com on Feb. 7, 2016.*
Tena et al., "Deposition of Inhaled Particles in the Lungs", Arch Bronconeumol.,2012; pp. 240-246.*
Gaikward et al., "Self Emulsifying Drug Delivery System: An Approach to Enhance Bioavailability and Solid Self-Emulsifying Drug Delivery Systems: A Review", Deccan J. Pharmaceutics and Cosmetology, 2015, pp. 1-38.*
Behera et al., "Evaluation of susceptibility testing methods for polymyxin", Internationl Journal of Infectious Diseases, 2010, e596-e601.*
Pardeshi et al.,Solid lipid based nanocarriers: An overview, Acta Pharm. 2012, pp. 433-472.*
Fang et al., Nanostructure Lipid Carriers (NLCs) for Drug Delivery and Targeting, Recent Patents on Nanotechnology, Jan. 2013, pp. 41-55.*
MSDS—Stearic Acid by Science Lab.com, created Oct. 11, 2005; pp. 1-5; obtained from www.sciencelab.com/msds.php?msdsId=9927609 on 08/06/1.*
Miglyol® 812 MSDS by Caelo; printed 2016, pp. 1-3; obtained from www.caelo.de on Aug. 6, 2017.*
Pardeshi et al. "Solid lipid based nanocarriers: An overview", Acta Pharm. 2012, pp. 433-472.*

(Continued)

*Primary Examiner* — Lianko G Garyu
(74) *Attorney, Agent, or Firm* — Edell, Shapiro & Finnan, LLC (57) ABSTRACT

A lipid nanoparticle that includes at least one antibiotic from the polymyxin family, a lipid fraction, and one or more surfactants. The lipid nanoparticle is useful in the prevention and/or treatment of respiratory tree infections.

22 Claims, 3 Drawing Sheets

(56) References Cited

OTHER PUBLICATIONS

PCT International Search Report and Written Opinion, PCT/ES2014/070538, Aug. 13, 2014, 7 pages.
Pattani et al., Development and Comparative Anti-Microbial Evaluation of Lipid Nanoparticles and Nanoemulsion of Polymyxin B, Journal of Nanoscience and Nanotechnology, vol. 6, (2006), pp. 2986-2990.

* cited by examiner

LIPID NANOPARTICLE OF POLYMYXIN

CROSS-REFERENCE TO RELATED APPLICATIONS

This application relates to and claims the benefit and priority to International Application No. PCT/ES2014/070538, filed Jul. 2, 2014, which claims the benefit and priority to European Application No. 13382268.4, filed Jul. 3, 2013.

TECHNICAL FIELD

The present invention is related to a lipid nanoparticle comprising at least one antibiotic from the polymyxin family, a pharmaceutical composition comprising said nanoparticle and the use of the nanoparticle in the prevention and/or treatment of respiratory tree infections.

BACKGROUND

One of the diseases on which chronic and recurring infections due to multidrug-resistant Gram negative bacteria (MDRGNB), for example, due to *Pseudomonas aeruginosa*, have the greatest effect is cystic fibrosis. The persistence of this bacterium is associated, among other causes, with its growth on a biofilm, consisting of a collective structure of bacteria that adheres to surfaces, coated with a protective layer secreted by the bacteria themselves, and providing the capacity to more effectively resist biocides and antibiotics, withstanding considerably higher doses of antibacterial products and causing pulmonary function impairment.

Some antibiotics for the treatment of these infections have adverse effects so the use of microsystems or nanosystems for administering said antibiotics is of particular interest. The literature describes different uses of these systems comprising some of these antibiotics, such as document US2009169635, which describes polyester type biodegradable polymeric nanoparticles for systemic administration.

Given that the local concentration of antimicrobial or antibiotic agents in the lung is one of the most important factors for the successful eradication of bacteria, the alveolar and bronchial epithelium seems to be the most interesting place for drug release.

The direct administration of antibiotics into the lower airways by means of the administration of aerosols and dry powder has potential advantages such as the higher local concentration that can be achieved by means of deposition in the alveolar location where the infection is, and therefore inhaled drugs can reduce the onset of systemic adverse effects since the administered dose is reduced.

Polymyxins are a family of antibiotics that were marketed in the 1950s and 1960s but later fell into disuse due to their adverse effects and to the emergence of other antibiotics specific for Gram negative bacteria (Shedding light on the use of colistin: still gaps to be filled. *Enfermedades Infecciosas y Microbiologia Clinica*, 2011, Volume 29, Issue 4). In recent years, due to the increase in infections caused by MDRGNB bacteria together with the absence of therapeutic alternatives, the use of the antibiotics from the polymyxin family is again on the rise. Nevertheless, the little clinical data available about their efficacy and safety make it difficult to assure whether the dosage regimens used today are the most suitable.

In view of this data, there is accordingly a need to develop medicaments for the treatment of respiratory tree infections that overcome the drawbacks of the state of the art.

SUMMARY OF THE DISCLOSURE

The inventors have developed lipid nanoparticles comprising at least one antibiotic from the polymyxin family that are able to adhere to or interact with the mucosal layer of the respiratory tract or the biofilm generated by the bacteria themselves, which favors obtaining optimal minimum inhibitory concentration results at a lower therapeutic dose of the antibiotic.

The nanoparticles are protected against premature degradation and furthermore present a sustained release of the antibiotic into the alveolar and bronchial epithelium.

Therefore, one aspect is to provide a lipid nanoparticle comprising at least one antibiotic from the polymyxin family, a lipid fraction comprising one or more lipids selected from the group consisting of monoglycerides and/or diglycerides and/or triglycerides and/or fatty acids and/or mixtures thereof.

Another aspect is related to a pharmaceutical composition comprising the lipid nanoparticles defined above together with one or more pharmaceutically acceptable excipients or carriers.

Another aspect is related to a method of preparing the lipid nanoparticles defined above comprising the following steps:
 a) Preparing a solution/mixture with the lipid fraction together with at least one antibiotic in an organic solvent.
 b) Preparing an aqueous solution with one or more surfactants.
 c) Mixing the oily phase a) and the aqueous phase b) to obtain an emulsion.
 d) Leaving the solvent to evaporate.
 e) Washing the obtained nanoparticles by means of centrifugation and/or ultrafiltration.

Another aspect is related to the lipid nanoparticle defined above for use as a medicament.

Another aspect is related to a method of preparing the lipid nanoparticles defined above comprising the following steps:
 a) Preparing a mixture of the lipids and at least one antibiotic by heating to a temperature slightly higher than the melting point of the solid lipid.
 b) Preparing an aqueous solution with one or more surfactants.
 c) Heating the aqueous solution b) to the same temperature as the oily phase a).
 d) Adding the aqueous phase b) to the oily phase a) and mixing to obtain an emulsion.
 e) Maintaining at a temperature of 5° C.±3° C. until the lipids recrystallize, giving rise to the nanoparticles.
 f) Washing the obtained nanoparticles by means of centrifugation and/or ultrafiltration.

The lipid nanoparticles can be useful in the treatment of infections, particularly respiratory tree infections. Therefore, another aspect of the invention is related to the lipid nanoparticle defined above for use as a medicament.

Another aspect is related to the lipid nanoparticle defined above for use in the treatment and/or prevention of respiratory tree infections. This aspect is therefore related to the use of the lipid nanoparticle defined above for preparing a medicament for the treatment and/or prevention of an infection, preferably respiratory tree infection, preferably caused by *P. aeruginosa* and/or related species and/or microorganisms sensitive to polymyxins.

Another aspect is related to a method of treating and/or preventing an infection, preferably a respiratory tree infection, preferably caused by *P. aeruginosa* and/or related species and/or microorganisms sensitive to polymyxins, which comprises administering a therapeutically effective amount of the lipid nanoparticle defined above, together with pharmaceutically acceptable excipients or carriers, in a subject in need of that treatment and/or prevention, including a human being.

In this sense, the studies conducted by the inventors have demonstrated the capacity of these lipid nanoparticles, as well as the pharmaceutical compositions and/or the medicaments comprising these nanoparticles, for:
- obtaining a stable lipid nanoparticle with a sustained and/or regulated release effect of the antibiotic,
- protecting the antibiotic against premature degradation,
- obtaining a particle size suitable for administration in the respiratory tract,
- having the capacity to penetrate the biofilm generated by the bacteria themselves, and
- obtaining better safety and efficacy values than the free antibiotic.

These and other advantages and features will become evident in view of the drawings and of the detailed description.

DETAILED DESCRIPTION

The lipid nanoparticle developed by the inventors comprises at least one antibiotic from the polymyxin family, a lipid fraction comprising one or more lipids selected from the group consisting of monoglycerides and/or diglycerides and/or triglycerides and/or fatty acids and/or mixtures thereof and one or more surfactants.

In the context of the present invention, the term "lipid nanoparticle" refers to a matrix comprising a lipid and/or lipophilic core, preferably a solidified lipid core, that could comprise nanocompartments containing the lipid in liquid state, surrounded by a hydrophilic phase encapsulating the core.

Nanoparticles comprising solid lipids at room temperature, also known as solid lipid nanoparticles, and nanostructured lipid carriers, which comprise a mixture of solid lipids and liquid lipids at room temperature, are included in the scope of the invention.

In a particular embodiment, the nanoparticles are characterized by having an average size between about 10 nm and about 1000 nm, preferably between about 100 nm and about 500 nm.

"Average size" is understood as the average diameter of the population of lipid nanoparticles. The average size can be measured by standard methods known by the person skilled in the art and described, for example, in the example section below.

Particle size is one of the factors determining the sustained release of the antibiotic. Generally, the antibiotic located on the nanoparticle surface is the first to be released. The smaller the nanoparticle size, the larger the specific interaction surface it has, so there would be a greater initial release of antibiotic.

In another embodiment, the nanoparticles have a surface charge (according to the Zeta potential measurement), the magnitude of which can range from about −30 mV to about −5 mV, and preferably between −30 mV and −16 mV. Generally, surface charge is one of the parameters affecting lipid nanoparticle stability. The fact that they are negatively or positively charged will favor the repulsive forces between nanoparticles in preventing cakings, presenting better dispersion properties.

Considering the positive charge of the lipopolysaccharides of the bacterial membranes present in the biofilm generated by the bacteria themselves and/or present in the pulmonary mucosa, the negative surface charge of the nanoparticles favor the nanoparticle-bacterium binding, optimizing the retention and adhesion of the nanoparticle in the site of action, favoring a better sustained and therapeutic effect of the antibiotic.

In another embodiment, the nanoparticles have polydispersity index (PDI) values equal to or less than 0.5. This index provides an idea as to the diversity of nanoparticle sizes existing in a mixture. The closer it is to zero, the more homogenous the nanoparticles are, which is indicative of a homogenous size distribution of the manufactured batches.

The mean size, Zeta potential and the PDI value of the nanoparticles are primarily affected by the amount of lipid component, by the amount of surfactants and by the parameters of the method of preparation, such as the strength and type of stirring, the temperature of both phases or the duration of the mixing phase.

Lipid Fraction

In a particular embodiment, the lipid nanoparticle comprises at least one solid lipid at room temperature forming part of the nanoparticle core as the lipid fraction.

For the purposes of the invention, room temperature is 20-25° C. Nevertheless, in the context of the present invention, "solid lipid at room temperature" is understood as that lipid that remains in solid form under 45° C., being able to be saturated or unsaturated. Said definition can include, without limitation, triglycerides (for example tristearin), and/or mono- or diglycerides (for example derivatives and mixtures of mono- and diglycerides) and/or fatty acids (for example stearic acid) or their derivatives and/or their mixtures, steroids (for example cholesterol) and waxes (for example cetyl palmitate). Each fatty acid of these glycerides and the fatty acids separately are normally characterized by having chains of between 10 and 28 carbon atoms. Those fatty acids, their esters or their amides having hydroxyl groups as substituents of the hydrocarbon chain are included in the definition of derivatives of fatty acids.

In a particular embodiment, the lipid fraction comprises a mixture of monoglycerides, diglycerides and/or triglycerides.

In one embodiment, the lipid fraction comprises a mixture of monoglycerides, diglycerides and triglycerides of glyceryl palmitostearate (for example, Precirol® ATO 5).

In another particular embodiment, the lipid fraction of the nanoparticle comprises a mixture of one or more solid lipids at room temperature and one or more liquid lipids at room temperature.

In the context of the present invention, "liquid lipid at room temperature" is understood as that lipid that remains in liquid form under 45° C., being able to be saturated or unsaturated. Said definition can include, without limitation, oils, and/or triglycerides, and/or monoglycerides and/or diglycerides and/or fatty acids and/or fatty acid esters and/or their mixtures. Each fatty acid of these glycerides and the fatty acids separately are normally characterized by having chains of less than 10 carbon atoms.

In a particular embodiment, the liquid lipid fraction comprises triglycerides.

In one embodiment, a caprylic acid triglyceride and a capric acid triglyceride (for example Miglyol® 812) is used as a liquid lipid.

The liquid lipid provides a less orderly structure, increasing the antibiotic load capacity in the nanoparticle core.

Figure 1:
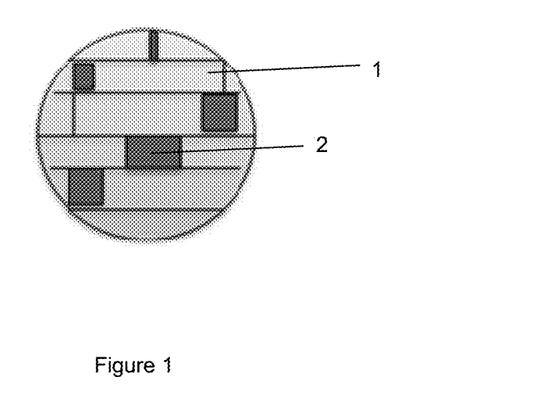
FIG. 1 shows a graphical depiction of lipid nanoparticles loaded with antibiotic in which the lipid fraction comprises solid lipids at room temperature.
Figure 2:
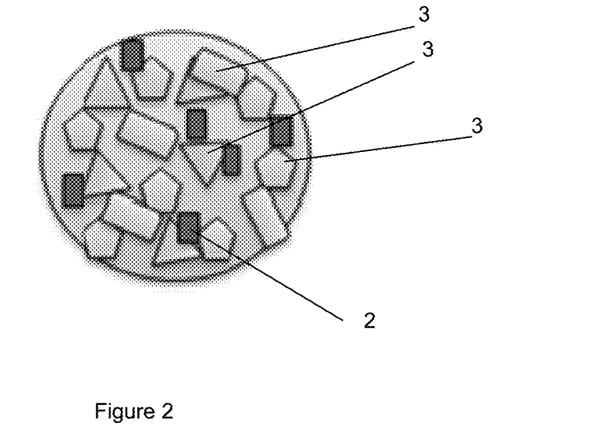
FIG. 2 shows a graphical depiction of lipid nanoparticles loaded with antibiotic in which the lipid fraction comprises a mixture of solid lipids at room temperature and liquid lipids at room temperature.
Figure 3:
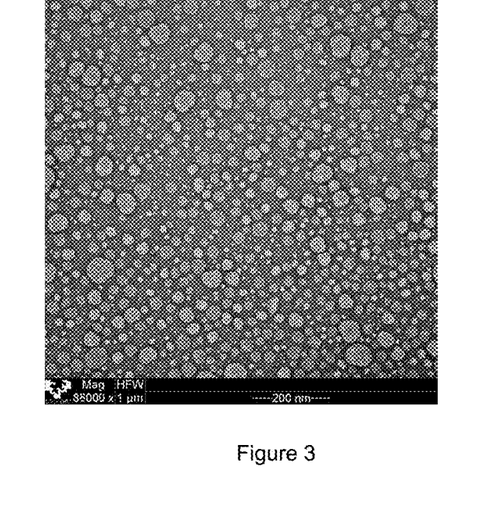
FIG. 3 shows a microscope photograph of an embodiment of lipid nanoparticles.

FIGS. 1 and 2 show a graphical depiction of particular examples of the lipid nanoparticles where FIG. 1 comprises solid lipids 1 together with the antibiotic 2, and FIG. 2 comprises a mixture 3 of solid and liquid lipids together with the antibiotic 2.

In one embodiment the weight ratio (weight/weight) of liquid lipid with respect to solid lipid is comprised between about 0.5:10 and about 5:10.

In another embodiment the weight ratio (weight/weight) of liquid lipid with respect to solid lipid is about 1:10.

The use of solid and liquid lipids provides the following advantages to the nanoparticle:
- improved tolerance in the organism and tissues due to the use of physiologically accepted lipids,
- possibility of encapsulating both lipophilic and hydrophilic drugs using different methods of preparation,
- they do not show biological toxicity, and
- it is possible to modulate the release of the antibiotic according to needs. Nanoparticles with a coating rich in antibiotic have a significant initial release while nanoparticles with a core rich in drug allow sustained release thereof.

Surfactant

As previously stated, the nanoparticles may comprise one or more surfactants. In a particular embodiment, the hydrophilic phase of the nanoparticles surrounding the lipophilic core comprises a surfactant. In the context of this invention, a surfactant is an emulsifier or emulsifying agent reducing the surface tension of the different phases required for manufacturing nanoparticles, achieving better interposition thereof and, therefore, nanoparticle formation.

The surfactants can be cationic, ionic or non-ionic, and they are classified according to their surface charge. Examples of cationic surfactants include, without limitation, cetrimide and/or cetylpyridinium chloride; examples of anionic surfactants include, without limitation, docusate sodium, phospholipids and/or sodium lauryl sulfate.

The term "non-ionic surfactant" is understood as that compound without any net charge, having a hydrophobic part and a hydrophilic part.

In one embodiment, the nanoparticle comprises at least one non-ionic surfactant the main functions of which are to control particle size and to confer stability preventing the formation of aggregates. Examples of non-ionic surfactants include, without limitation, polysorbates, polyethylene glycol co-polymers and/or polypropylene glycol co-polymers.

In a preferred embodiment, the non-ionic surfactants are polysorbate 80 and/or poloxamer.

In a particular embodiment, the non-ionic surfactant proportion is comprised between 0.5% and 2% by weight with respect to the total weight of the nanoparticle, preferably 1%.

Antibiotic

An antibiotic or antimicrobial agent is an agent that acts against bacterial infections by either inhibiting bacterial growth or by giving rise to a chain of biochemical events that will result in bacterial lysis.

The lipid nanoparticle comprises at least one antibiotic from the polymyxin family such as polymyxin A, polymyxin B, polymyxin C, polymyxin D and polymyxin E.

In a one embodiment, the lipid nanoparticle comprises at least one antibiotic of the colistin or colistimethate sodium type.

The release of the antibiotic as well as the antibacterial action can be regulated by means of the weight ratio of the antibiotic with respect to the lipid fraction. In a particular embodiment, the weight ratio of the antibiotic with respect to the lipid fraction is from about 0.25:10 to about 4:10, preferably being about 1:10.

The antibacterial action of an antibiotic can be measured by means of the minimum inhibitory concentration, which consists of the concentration of the antibiotic required to prevent bacterial growth after the incubation of $10^{4-5}$ bacteria in rapid growth phase, in an aerobic, protein-free medium with pH 7.2 for an incubation period of one night. This term is used to determine the sensitivity of the bacteria to a specific antibiotic agent.

In the context of infection, the term "sensitive" means inhibition of the growth of the microorganism and/or death of the microorganism in the case of a treatment at the therapeutic dose.

The weight ratios of the antibiotic-lipid fraction of the different embodiments disclosed herein have demonstrated a minimum inhibitory concentration that is lower than the free antibiotic. This fact, in addition to being an advantage in terms of costs because a smaller amount of antibiotic is required for the same therapeutic effect, favors a lower probability of acquired bacterial resistances.

In the context of the invention, the term "acquired bacterial resistance" is understood as that resistance acquired by the bacterium through the acquisition of resistance genes from other bacteria and/or through mutation processes. Bacterial resistance is directly related, among other causes, with the use of unsuitable doses or durations of antibacterial therapy.

Method of Preparation

The lipid nanoparticles of the present invention can be prepared by means of the solvent emulsification/evaporation technique or by means of the hot melt homogenization technique.

The first technique may comprise the following steps:
a) Preparing a solution/mixture with the lipid fraction together with at least one antibiotic in a solvent organic.
b) Preparing an aqueous solution with one or more surfactants.
c) Mixing the oily phase a) and the aqueous phase b) to obtain an emulsion.
d) Leaving the solvent to evaporate.
e) Washing the obtained nanoparticles by means of centrifugation.

In a particular embodiment, the lipid fraction is dissolved in an organic solution between 1 and 10% (weight/volume), preferably between 3 and 7%, and more preferably at 5%, together with at least one antibiotic. On the other hand, an aqueous solution with at least one surfactant is prepared. The aqueous phase is added to the oily phase, and the mixture is emulsified by means of sonication for a specific time. The nanoparticle size, polydispersity index and encapsulation efficiency will depend on sonication power and sonication time. It is preferably sonicated between 10 W and 30 W, and more preferably between 15 W and 25 W, for between 15 seconds and 40 seconds, preferably between 25 seconds and 35 seconds, and more preferably between 29 seconds and 31 seconds. Once the emulsion is obtained, the solvent is allowed to evaporate under magnetic stirring for two hours at room temperature. After evaporation, the obtained nanoparticles are washed by centrifuging and filtering between 1 and 10 times, preferably between 2 and 5 times, and more preferably 3 times.

The second technique may comprise the following steps:
a) Preparing a mixture of the lipids and at least one antibiotic by heating to a temperature slightly higher than the melting point of the solid lipid.
b) Preparing an aqueous solution with one or more surfactants.
c) Heating the aqueous solution b) to the same temperature as the oily phase a).
d) Adding the aqueous phase b) to the oily phase a) and mixing to obtain an emulsion.
e) Maintaining at a temperature of 5° C.±3° C. until the lipids recrystallize.
f) Washing the obtained nanoparticles by means of centrifugation/ultrafiltration.

In a particular embodiment, on one hand the solid and/or liquid lipids and the antibiotics are mixed together and heated to a temperature slightly higher than the melting point of the solid lipid. On the other hand, an aqueous solution with at least one surfactant is prepared. The oily solution and the aqueous solution are heated to the same temperature, and the aqueous solution is added to the oily solution once both phases reach the same temperature. The mixture is emulsified by means of sonication. As in the preceding method, the nanoparticle size, polydispersity index and encapsulation efficiency depend of sonication power and sonication time. It is preferably sonicated between 10 W and 30 W, and more preferably between 15 W and 25 W, for between 10 seconds and 30 seconds, preferably between 12 seconds and 16 seconds, and more preferably between 14 seconds and 15 seconds. According to some embodiments the obtained emulsion is stored between 5 hours and 30 hours at temperature between 1° C. and 10° C., preferably between 2° C. and 6° C., and more preferably between 3° C. and 5° C. According to some embodiments the obtained emulsion is stored between 10 hours and 20 hours at temperature between 1° C. and 10° C., preferably between 2° C. and 6° C., and more preferably between 3° C. and 5° C. According to some embodiments the obtained emulsion is stored for 12 hours at temperature between 1° C. and 10° C., preferably between 2° C. and 6° C., and more preferably between 3° C. and 5° C. The lipids recrystallize in this period forming the nanoparticles. Once the time has lapsed, the nanoparticles are washed by centrifuging and filtering between 1 and 10 times, preferably between 2 and 5 times, and more preferably 3 times, between 1000 rpm and 3500 rpm, preferably at 2000 rpm to 3000 rpm and more preferably at about 2500 rpm for between 10 minutes and 30 minutes, preferably between 12 minutes and 16 minutes, and more preferably between 14 minutes and 15 minutes. One of the advantages of this method is that organic solvents are not used, thereby preventing the need to conduct tests for determining traces of organic solvents before commercialization of the nanoparticles for human consumption.

One aspect is related to the product obtainable by the techniques described above.

Lyophilization

In a particular embodiment, the lipid nanoparticle is a lyophilized nanoparticle. Lyophilization allows obtaining a dry powder containing the lipid nanoparticles, which provides it with greater stability than lipid nanoparticles in suspension, since it prevents nanoparticle degradation and the early release of the antibiotic into the solution in which the nanoparticles are suspended.

Lyophilization can be performed by standard methods known by the person skilled in the art and described, for example, in the examples section below.

In one embodiment, the lipid nanoparticle comprises a cryoprotectant. The cryoprotectant favors nanoparticle stabilization during the freezing process of the lyophilization process. This cryoprotectant can be selected, without limitation, from colloidal $SiO_2$, glycine, lactose, mannitol, trehalose, raffinose, sodium bicarbonate and sodium borate.

In one embodiment, the nanoparticle comprises trehalose as a cryoprotectant.

In one embodiment, the lipid nanoparticle comprises between about 5% and about 20% by weight of cryoprotectant with respect to the weight of the lipid nanoparticle, preferably between 5% and 15%.

Infection

One aspect of the invention is related to the use of the lipid nanoparticle in the treatment and/or prevention of infection, preferably a respiratory tree infection.

Another aspect is related to the use of the lipid nanoparticle for preparing a medicament for the treatment and/or prevention of infection, preferably a respiratory tree infection.

Another aspect is related to a method of treatment or prevention of an infection, preferably a respiratory tree infection, which comprises administering a therapeutically effective amount of the lipid nanoparticle defined above, together with pharmaceutically acceptable excipients or carriers, in a subject in need of that treatment and/or prevention, including a human being.

The term "infection" includes any infection by Gram negative bacteria and/or bacteria or microorganisms sensitive to the antibiotics of the polymyxin family.

The term "respiratory tree" includes the nasal cavity, pharynx, larynx, trachea, main bronchus and lungs.

In the context of the specification, the term "prevention or treatment" means the administration of the nanoparticles to preserve the health of a patient who is suffering or who is at risk of suffering a bacterial infection described above. Said terms also include the administration of the nanoparticles to prevent, improve, alleviate or eliminate one or more symptoms associated with bacterial infection. In the context of this invention, the term "improve" is understood to mean any improvement in the situation of the treated patient, that is either a subjective improvement (how the patient feels) or an objective improvement (measured parameters).

In a particular embodiment, the infection in the respiratory tree is caused by *Pseudomonas aeruginosa.*

The nanoparticle has demonstrated its capacity to adhere to the biofilm generated by the bacterium or the actual mucous of the respiratory tree tissue. Therefore a particular embodiment is related to the use of the lipid nanoparticle in pulmonary infection associated with cystic fibrosis and/or bronchiectasis.

The lipid nanoparticles can form part of a pharmaceutical composition. Said pharmaceutical compositions include any solid, semi-solid or liquid composition for oral (enteral, sublingual or rectal), topical (transdermal or ophthalmic), parenteral (intradermal, subcutaneous, intramuscular, intravenous or intraperitoneal) application or for direct administration in the respiratory tree.

The pharmaceutical composition comprises the lipid nanoparticle together with pharmaceutically acceptable excipients or carriers, in a subject in need of that treatment and/or prevention, including a human being. The person skilled in the art can determine what additional components can be used and if they are necessary, many of them being commonly used in pharmaceutical compositions.

In the context of this invention, the expression "therapeutically effective amount" refers to the amount of composition which is sufficient for preventing or treating one or more symptoms derived from bacterial infection once administered. The particular dose administered according to the present invention will be determined according to the particular circumstances surrounding the case, including the administered compound, the administration route, the particular condition being treated and similar considerations.

The expression "pharmaceutically acceptable excipients or carriers" refers to pharmaceutically acceptable materials, composition or vehicles. Each component must be pharmaceutically acceptable in the sense of being compatible with the other ingredients of the pharmaceutical composition. It must also be suitable for use in contact with human and animal tissues or organs without excessive toxicity, irritation, allergic reaction, immunogenicity or other problems or complications in accordance with a reasonable risk-benefit ratio.

The pharmaceutical composition can comprise other ingredients such as viscosity modulators, preservatives, solubilizers including, without limitation, cyclodextrins, lecithins and/or glycerol monostearate, anti-flocculants including, without limitation, leucine, and/or stabilizers including, without limitation, alginates, alginic acid and/or trehalose. These components will be added to the lipophilic or hydrophilic phase depending on the nature of said components.

In a particular embodiment, the pharmaceutical composition comprises the lipid nanoparticles of polymyxin, a cryoprotectant, an anti-caking agent and other excipients. The pharmaceutical presentation can be a powder to be nebulized in solution or in dry powder for direct administration.

In one embodiment, it is administered by means of inhaling into the respiratory tract.

These administrations by means of inhaling are liquid or solid preparations containing the nanoparticle and/or pharmaceutical composition and/or medicament of the invention alone or together with more drugs. The size of the particles intended to be inhaled must be suitable for them to be distributed in the lower part of the respiratory tree and controlled by methods suitable for determining particle size. The person skilled in the art can determine the processes and/or devices that can be applied for an optimal administration by means of vapors or aerosols or powders.

In another aspect the inhaled particle size is comprised between 1 μm and 10 μm, preferably between 2 μm and 8 μm, and more preferably between 3 μm and 5 μm. These sizes allow perfect alveolar deposition and lung retention of the therapeutically effective amount. In a particular embodiment, these sizes are obtained by aggregating the nanoparticles if they are applied as a dry powder, or by generating a spray with the suitable carrier if they are administered by means of nebulization.

Some illustrative examples which clearly show the features and advantages are described below. However, these examples must not be interpreted as limiting the scope of the invention.

EXAMPLES

Example 1: Preparation of Lipid Nanoparticles with Antibiotic by Means of Solvent Emulsification/Evaporation Technique

Example 1a 10 mg of colistimethate sodium were mixed in a 100 mg solution of 5% glyceryl distearate (for example Precirol® ATO 5) in dichloromethane (final volume of 2 mL).

An aqueous solution of surfactants (1% Poloxamer 188 and 1% Polysorbate 80) was also prepared. The aqueous phase was added to the oily phase, and the mixture was emulsified by means of sonication at 20 W for 30 seconds. It was then left under magnetic stirring for two hours so that the solvent evaporated.

After evaporation, the obtained nanoparticles were washed by centrifuging 3 times at 2500 rpm for 15 minutes using Amicon® Ultra (Millipore) filters.

Example 1b

Some of these nanoparticles were lyophilized, subjecting them to the following steps:

a) Adding 15% trehalose with respect to the total weight of the lipid fraction.

b) Freezing at −20° C. and then at −80° C.

c) Freezing at −50° C. at a pressure of 10,000 mbar for 3 hours.

d) Applying a vacuum at −50° C. until obtaining a pressure of 0.20 mbar.

e) Drying at −50° C. at a pressure of 0.20 mbar for 5 hours.

f) Drying at 20° C. at a pressure of 0.20 mbar for 7 hours.

g) Drying at 20° C. at ambient pressure for 24 hours.

Example 2: Preparation of Lipid Nanoparticles with Antibiotic by Means of Hot Melt Homogenization Technique

Example 2a

A mixture of 1000 mg of Precirol® ATO 5 and Miglyol® 812 was prepared at a ratio of 10:1 together with 100 mg of colistimethate sodium at a temperature slightly higher than the melting point of the solid lipid.

An aqueous solution of surfactant (0.6% Poloxamer 188 and 1.3% Polysorbate 80) was also prepared.

The lipid solution and the aqueous solution were heated to the same temperature (to a temperature between about 5° C. and 10° C. higher than the melting temperature of the lipids).

The aqueous phase was added to the oily phase, and the mixture was emulsified by means of sonication at 20 W for 15 seconds. The obtained emulsion was stored for 12 hours at 4° C. so that the lipids could recrystallize and form the nanoparticles.

The obtained nanoparticles were washed by centrifuging 3 times at 2500 rpm for 15 minutes using Amicon® Ultra (Millipore) filters.

Example 2b

Some of these nanoparticles were lyophilized, subjecting them to the steps mentioned in Example 1b.

Example 3 (Reference Example): Preparation of Lipid Nanoparticles without Antibiotic Several batches of lipid nanoparticles without antibiotic, with different weight ratios of liquid lipid with respect to solid lipid, were prepared according to the method described in Example 2. The ratios were: 0.5:10; 1:10; 2.5:10 and 5:10.

Example 4 Characterization of the Nanoparticles

The particle size and the Zeta potential were characterized by means of a Zetasizer Nano ZS. The following table describes the mean results obtained with the batches manufactured according to Examples 1, 2 and 3:

| Batches | Liquid lipid-solid lipid ratio | Size (nm) | Zeta Potential (mV) | Polydispersity index (PDI) |
|---|---|---|---|---|
| Example 1a | 0:10 | 196 ± 20 | −20 ± 1 | 0.27 |
| Example 1b | 0:10 | 303 ± 39 | −21 ± 2 | 0.27 |
| Example 2a | 1:10 | 219 ± 23 | −24 ± 1 | 0.33 |
| Example 2b | 1:10 | 500 ± 42 | −23 ± 2 | 0.55 |
| Example 3 | 0.5:10 | 397 ± 44 | −16 ± 1 | 0.35 |
| Example 3 | 1:10 | 248 ± 46 | −25 ± 2 | 0.38 |
| Example 3 | 2.5:10 | 401 ± 56 | −31 ± 2 | 0.46 |
| Example 3 | 5:10 | 396 ± 56 | −31 ± 1 | 0.46 |

It can be observed from this table that nanoparticles with a size, Zeta potential and PDI that are optimum for good nanoparticle stability and homogeneity were obtained.

Example 5: Encapsulation Efficiency

The antibiotic encapsulation efficiency was determined by determining the amount of antibiotic present in the supernatant after the washing process described in Examples 1 and 2. The antibiotic present in the supernatant was analyzed by HPLC using a Waters 1525 HPLC Binary Pump (Waters Corp., Milford, USA), a Waters 2487 ultraviolet detector and a Waters 717 plus automatic injector. The system was controlled by the Empower software. The selected column was Novapak C 18×150 mm with a pore size of 4 μm.

The mobile phase was made up of a 77% aqueous solution and of 23% acetonitrile. The aqueous phase was prepared by dissolving (7.1 g) sodium sulfate, (0.6 g) acetic acid and (2.2 g) phosphoric acid and adjusted to pH 2.5 with triethylamine for 1 liter of aqueous solution. Colistimethate sodium was detected at a wavelength of 206 nm. The flow rate was 1.5 ml/min for an isocratic elution. 50 μl of sample dissolved in water were injected. It was observed that the assay was linear for 100-800 μg/ml, no interference being detected.

The encapsulation efficiency was determined using the following formula:

$$EE\ (\%) = 100 * (\text{initial amount of antibiotic} - \text{amount of non-encapsulated antibiotic})/\text{initial amount of antibiotic}.$$

The batches manufactured according to the method of manufacture described in Example 1 gave mean values of 80±7%, and the batches manufactured according to the method described in Example 2 gave mean values of 95±4%. These values are indicative that the effectiveness of the method of preparation has values close to 100%, assuring maximum use of the antibiotic added to the process of manufacture.

Example 6: In Vitro Assays for Determining the Minimum Inhibitory Concentration (MIC)

100 μl of a concentration of $10^4$ Colony Forming Units (CFU)/ml of 31 *P. aeruginosa* strains obtained from 31 patients with cystic fibrosis, 13 strains of which were mucus producers, were incubated for 24 hours at 37° C. in a Mueller Hinton broth, cation-adjusted (MHBCA) medium, corresponding to between 20 mg and 25 mg per liter of calcium and between 10 mg and 12.5 mg per liter of magnesium, assuring the reproducibility of the results for *P. aeruginosa*, in the presence of colistimethate sodium, and nanoparticles obtained according to Examples 1b and 2b, at different concentrations (less than 0.25, 0.25, 0.5, 1, 2, 4, 8 and 32 μg/ml).

For colistimethate sodium, an MIC of 2 μg/ml was obtained for 48% of the strains, an MIC of 1 μg/ml was obtained for 25% of the strains and an MIC of 0.5 μg/ml was obtained for 16% of the strains. An MIC of 4 μg/ml was obtained for the remaining strains.

In the case of the nanoparticles obtained according to Example 1b, an MIC of 2 μg/ml was obtained for 52% of the strains, an MIC of 1 μg/ml was obtained for 25% of the strains, an MIC of 0.5 μg/ml was obtained for 13% of the strains and an MIC of less than 0.25 μg/ml was obtained for 3% of the strains. An MIC of 4 μg/ml was obtained for the remaining strains.

In the case of the nanoparticles obtained according to Example 2b, an MIC of 1 μg/ml was obtained for 42% of the strains, an MIC of 0.5 μg/ml was obtained for 23% of the strains, an MIC of 0.25 μg/ml was obtained for 10% of the strains, an MIC of less than 0.25 μg/ml was obtained for 3% of the strains, an MIC of 2 μg/ml was obtained for 16% of the strains and an MIC of more than 4 μg/ml was obtained for the remaining strains.

These results demonstrate that the nanoparticles of the present invention have a better MIC value than the free antibiotic.

Example 7: Release Studies

Figure 4:
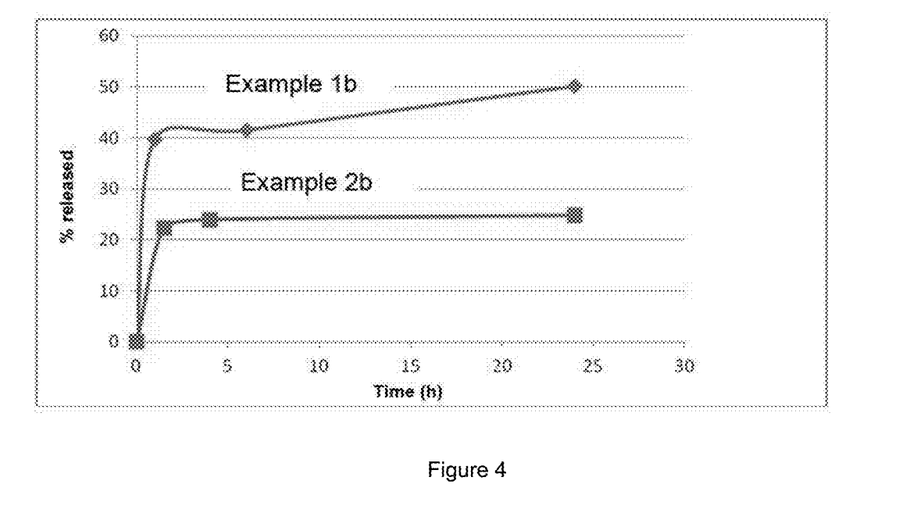
FIG. 4 shows an antibiotic release curve over time of the lipid nanoparticles.

On one hand, a sample of 25 mg of nanoparticles prepared according to the method described in Example 1b was incubated, and on the other hand, a sample of 25 mg of nanoparticles prepared according to the method described in Example 2b was incubated, each being incubated in 5 ml of PBS. The samples were centrifuged using Amicon® Ultra (Millipore) filters for 15 minutes at pre-established times. The antibiotic present in the supernatant was analyzed by HPLC according to Example 5. The PBS removed by centrifugation was replaced with new PBS. FIG. 4 shows the percentage of released antibiotic with respect to the total amount of antibiotic encapsulated in the nanoparticle for each nanoparticle type over time (hours).

Given their size, the lipid nanoparticles have a large specific surface. When they are contacted with the PBS, first the drug associated with the nanoparticle surface or very close to the nanoparticle surface is released. This first rapid release phase is called a burst. In a second phase, the active ingredient is released by degradation/erosion or by swelling of the particle core, giving rise to the sustained release phase. In the case of antimicrobial therapy, the antibiotic levels were optimal for inhibiting growth of P. aeruginosa bacteria in vitro.

Example 8: In Vivo Toxicity Assays and Distribution of the Nanoparticles Manufactured According to Examples 1b and 2b in CD1 Mice To carry out the in vivo toxicity and efficacy assays of the nanoparticles of the present invention, it was necessary to establish a rodent infection model. An intratracheal administration of different concentrations of mucosa producing P. aeruginosa included in microspheres (Concentration 1: $5 \times 10^4$ CFU, Concentration 2: $2.4 \times 10^7$ CFU, and Concentration 3: $3.89 \times 10^{10}$), obtained from a patient with cystic fibrosis, suspended in PBS, in CD1 mice was carried out, administering a different concentration to each rodent, to establish the optimum concentration for generating a suitable pulmonary infection, capable of making the rodents sick without causing their immediate death. It was concluded that the optimum concentration was $2.4 \times 10^7$ CFU since the mice managed to survive for more than three days and it was confirmed after sacrificing them that they had a pulmonary infection.

A toxicity study of the nanoparticles manufactured according to Example 1b and Example 2b administered intratracheally was carried out. 1.2 mg of nanoparticles in 50 microliters of PBS (optimum amount to prevent excessive mixture density) were administered to a group of 16 CD1 mice, in addition to establishing the corresponding control groups (5 mice) to which no product was administered. Up to three days after the administration, all the mice presented standard behavior, responding to stimuli and moving normally. After those three days, the mice were sacrificed, a bronchoalveolar lavage was performed and lung samples were obtained and prepared for analysis for the anatomical-pathological study thereof. The study of the samples did not reveal any inflammation or damage in the studied tissues that may have been caused by the nanoparticles of the present invention.

Figure 5:
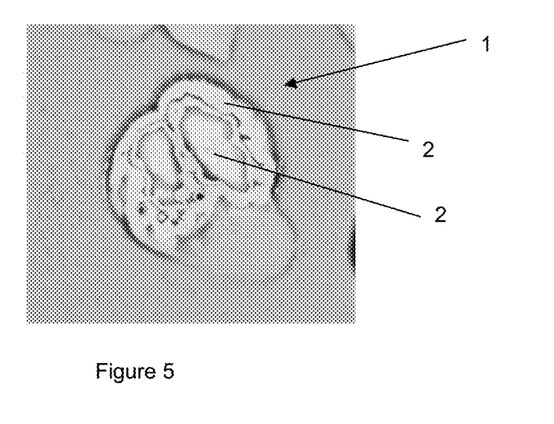
FIG. 5 shows an image of the pulmonary distribution of fluorescent microspheres after administration to a CD1 mouse.

Additionally, 6 µm microspheres in 50 µl (equivalent to those used for inducing infection) loaded with a fluorescent reagent or fluorophore (excitation wavelength: 630-660 nm and emission wavelength 670-720 nm) in order to enable assuring that the administration technique was effective and that the microspheres are effectively deposited on the lung for the most part, were administered. FIG. 5 shows an image of the lungs of a CD1 mouse after the intratracheal administration of $1 \times 10^6$ fluorescent microspheres. The animal was sacrificed 5 minutes after administering the microspheres. The microspheres (AlignFlow™ polystyrene microspheres 6.0 µm in diameter, λex: 630-660 nm, λem: 670-720 nm, Invitrogen) were administered resuspended in 50 µl of PBS. Localization was performed with a Pearl-Impulse imaging system (LI-COR Biosciences, USA). The image shows the homogenous distribution of the fluorescent reagent 2 in the entire lung 1 of the rodent.

Example 9: In Vivo Efficacy Assays in CD1 Mice of the Nanoparticles Manufactured According to Examples 1b and 2b Five mice were used as the control group and 64 mice infected with the inoculation of the bacteria of a mucosa producing P. aeruginosa strain, at a concentration of $2.4 \times 10^7$ CFU, as explained in Example 8, were used. The infected animals were divided into 4 groups of eight, medium (PBS), the free antibiotic (colistimethate sodium), nanoparticles manufactured according to Example 3 and the equivalent amount of antibiotic in the form of nanoparticles manufactured according to Example 1b and Example 2b, respectively, being intratracheally administered to the animals on the third day after inoculation. The amounts were calculated by adjusting the dose recommended in humans with respect to the weight of the mice (3000 IU, equivalent to 0.24 mg of free colistimethate sodium, equivalent to 2.88 mg of the nanoparticles according to Example 1b and 2.52 mg of nanoparticles according to Example 2b).

Treatment was prolonged for three days, being administered once a day to prevent subjecting the mice to excessive harm due to the successive administration of anesthesia and intratracheal administration. Once this time has lapsed, the animals were sacrificed, the lungs extracted and homogenized, and an agar culture was prepared to enable carrying out a P. aeruginosa bacteria count. From the obtained results, it was concluded that the nanoparticles of the present invention have a greater bactericidal effect as a count significantly lower than that corresponding to free colistimethate was obtained. The following table details the results obtained for each case:

| Group | Bacterial count (log CFU for every 2 lungs) |
| --- | --- |
| Only medium | 6.7 ± 0.3 |
| Empty nanoparticles | 6.8 ± 0.2 |
| Free colistimethate sodium | 4.9 ± 0.2 |
| Nanoparticles according to Example 1b | 4.2 ± 0.2 |
| Nanoparticles according to Example 2b | 3.8 ± 03 |

Example 10: The Median Inhibition Concentration Value (IC50) Assay of the Nanoparticles Manufactured According to Examples 1b and 2b in Human Cells The median inhibition concentration value (IC50) refers to the concentration of an assayed sample required to inhibit the growth of the 50% of the cell population. In this case IC50 value was estimated as a toxicity marker, as the cell viability assay is run under human cell (A549 and H441 cell lines, which are immortalised lines derived from human adenocarcinomic epithelial cell). Cells (at a density of 12,000 cells per well in a 96-well plate) were grown in Dulbecco's Modified Eagle Medium (DMEM) supplemented with 10% foetal bovine serum (FBS), 1% L-glutamine, 1% penicillin/streptomycin solution and 1% of Minimum Essential Medium non-essential amino acids 100× (MEM-NEAA) at 37° C. and 5% $CO_2$ for 24 hours. Decreasing concentrations of nanoparticles 1b and 2b and free colistimethate sodium, starting from 10 mg/ml to 0.07812 mg/ml were added to the cells, diluted in DMEM supplemented with 0.5% serum and incubated at 37°±2° C. and 5% $CO_2$ for 24 h. Cell viability was assessed by means of the Cell Counting Kit 8 after a washing step. With this aim, 10% of CCK-8 reagent was added to each well and incubated in a wet chamber for 4 hours at 37°±2° C. and 5% $CO_2$. Subsequently, the absorbance was read at 450 nm and at 650 nm as the reference wavelength. The absorbance was directly proportional to the number of living cells in culture. The results are given as 50% of living cells, meaning that this dose inhibits the growth of the 50% of the population. The test was run in triplicate for each sample. This study revealed that nanoencapsulation of the antibiotic led to lower IC50 values, hence less toxic formulation. In addition, it should be also underlined that this IC50 values are above the 1 to 2 μg/ml reported as MIC. The following table details the results obtained for each case:

|  | H441 cell line | A549 cell line |
|---|---|---|
| Example 1b | 358.49 ± 73.86 μg/ml | 1309.97 ± 318.69 μg/ml |
| Example 2b | 1087.14 ± 197.43 μg/ml | 2821.57 ± 877.09 μg/ml |
| Free colistimethate sodium | 6.58 ± 0.72 μg/ml | 101.27 ± 14.44 μg/ml |

The invention claimed is:

1. A lipid nanoparticle comprising:
at least one antibiotic from the polymyxin family;
a lipid fraction comprising at least one lipid that is a solid at room temperature and at least one lipid that is a liquid at room temperature, wherein the solid lipid and the liquid lipid are each selected from the group consisting of:
(a) a monoglyceride;
(b) a diglyceride;
(c) a triglyceride;
(d) a fatty acid; and
(e) a mixture thereof; and
one or more surfactants,
wherein said nanoparticle has antibiotic located on the nanoparticle surface and in the nanoparticle core.

2. The lipid nanoparticle according to claim 1, wherein the weight ratio of the antibiotic with respect to the lipid fraction is between 0.25:10 and 4:10.

3. The lipid nanoparticle according to claim 1, wherein the weight ratio of the liquid lipid with respect to the solid lipid is between 0.5:10 and 5:10.

4. The lipid nanoparticle according to claim 1, wherein the weight proportion of the one or more surfactants with respect to the total weight of the nanoparticle is between 0.5% and 2%.

5. The lipid nanoparticle according to claim 1, wherein the one or more surfactants are non-ionic.

6. The lipid nanoparticle according to claim 1, wherein the antibiotic from the polymyxin family is selected from the group consisting of colistin and colistimethate sodium.

7. The lipid nanoparticle according to claim 1, further comprising a cryoprotectant.

8. The lipid nanoparticle according to claim 1, wherein the lipid nanoparticle is lyophilized.

9. The lipid nanoparticle according to claim 2, wherein the weight ratio of the antibiotic with respect to the lipid fraction is about 1:10.

10. The lipid nanoparticle according to claim 1, wherein the solid lipid is a solid under 45° C. and the liquid lipid is a liquid under 45° C.

11. The lipid nanoparticle according to claim 1, wherein the solid lipid is a solid at 20-25° C. and the liquid lipid is a liquid at 20-25° C.

12. The lipid nanoparticle according to claim 1, wherein the solid lipid is a solid above 45° C. and the liquid lipid is a liquid below 15° C.

13. The lipid nanoparticle according to claim 1, wherein the solid lipid forms a core of the lipid nanoparticle that encapsulates the antibiotic.

14. The lipid nanoparticle according to claim 1, wherein the encapsulation efficiency of the antibiotic by the lipid nanoparticle is at least 95%.

15. The lipid nanoparticle according to claim 1, comprising a solidified lipid core comprising nanocompartments containing the liquid lipid and the antibiotic.

16. A pharmaceutical composition comprising the lipid nanoparticle according to claim 1 together with one or more pharmaceutically acceptable excipients or carriers.

17. A lipid nanoparticle consisting essentially of:
(a) at least one antibiotic from the polymyxin family;
(b) a lipid fraction; and
(c) one or more surfactants;
wherein said lipid fraction comprises at least one lipid that is a solid at room temperature and at least one lipid that is a liquid at room temperature,
wherein the solid lipid and the liquid lipid are each selected from the group consisting of a monoglyceride, a diglyceride, a triglyceride, a fatty acid, and a mixture thereof.

18. The lipid nanoparticle according to claim 17, wherein the weight ratio of the antibiotic with respect to the lipid fraction is between 0.25:10 and 4:10.

19. A method of administering a therapeutically effective amount of a lipid nanoparticle to a patient in need thereof, comprising administering to said patient a therapeutically effective amount of is a nanoparticle according to claim 1.

20. The method of claim 19, wherein the lipid nanoparticle treats respiratory tree infections in the patient.

21. The method of claim 20, wherein the respiratory tree infections are caused by *Pseudomonas aeruginosa* and/or microorganisms sensitive to polymyxins.

22. The method of claim 21, wherein administration occurs by inhalation of the lipid nanoparticle into the respiratory tract, in the form of vapors or sprays or powders, wherein the inhaled particles have a size between 1 μm and 10 μm.

* * * * *